United States Patent
Kronberg et al.

(10) Patent No.: US 12,232,875 B2
(45) Date of Patent: Feb. 25, 2025

(54) NEUROLOGICAL ELECTRODE SYSTEM FOR MAGNETIC RESONANCE ENVIRONMENTS

(71) Applicant: RHYTHMLINK INTERNATIONAL, LLC, Columbia, SC (US)

(72) Inventors: James W. Kronberg, Columbia, SC (US); Harrison M. Floyd, Columbia, SC (US); Daniel E McCoy, Columbia, SC (US); Gabriel Orsinger, Columbia, SC (US)

(73) Assignee: Rhythmlink International, LLC, Columbia, SC (US)

( * ) Notice: Subject to any disclaimer, the term of this patent is extended or adjusted under 35 U.S.C. 154(b) by 9 days.

(21) Appl. No.: 17/491,721

(22) Filed: Oct. 1, 2021

(65) Prior Publication Data
US 2022/0079493 A1    Mar. 17, 2022

Related U.S. Application Data

(63) Continuation of application No. 17/021,044, filed on Sep. 15, 2020, now Pat. No. 11,160,483.

(51) Int. Cl.
*A61B 5/24* (2021.01)
*A61B 5/291* (2021.01)
(Continued)

(52) U.S. Cl.
CPC ............... *A61B 5/291* (2021.01); *A61B 5/30* (2021.01); *H01C 1/16* (2013.01)

(58) Field of Classification Search
CPC ... A61B 2562/164; A61B 5/4836; A61B 5/24; A61B 2562/0223; A61B 2562/04;
(Continued)

(56) References Cited

U.S. PATENT DOCUMENTS 2,894,197 A    7/1955    Berry
5,495,213 A    2/1996    Ikeda
(Continued)

FOREIGN PATENT DOCUMENTS

WO    9905893 A1    2/1999
WO    2015183620 A2    12/2015

OTHER PUBLICATIONS

International Search Report and Written Opinion issued in counterpart PCT Application No. PCT/US2020/013514 dated Apr. 24, 2020.

*Primary Examiner* — Deborah L Malamud
(74) *Attorney, Agent, or Firm* — Bryan L. Baysinger; Nicholas P. Stadnyk; Maynard Nexsen PC

(57) ABSTRACT

An electrode system includes an electrode, a connector, and a cable with an in-line radio-frequency filter module comprising resistors and inductors without any deliberately added capacitance. The resistors are arranged in an alternating series of resistors and inductors, preferably with resistors at both outer ends, and connected electrically in series. The in-line module is located at a specific location along the wire, chosen through computer modeling and real-world testing for minimum transfer of received RF energy to a patient's skin, such as between 100 cm and 150 cm from the electrode end of a 240 centimeter cable. The total resistance of the resistors plus cable, connectors and solder is 1000 ohms or less; while the total inductance is roughly 1560 nanohenries. The inductors do not include ferrite or other magnetic material and are, together with the resistors, stock components thereby simplifying manufacture and reducing cost.

23 Claims, 5 Drawing Sheets

(51) Int. Cl.
*A61B 5/30* (2021.01)
*H01C 1/16* (2006.01)

(58) Field of Classification Search
CPC ........ A61B 5/00; A61B 5/725; A61N 1/0551; A61N 1/08; A61N 1/36125; A61N 1/37223; A61N 1/0472; A61N 1/3606; A61N 1/375; A61N 1/00; A61N 1/3718; A61N 1/36128
See application file for complete search history.

(56) References Cited

U.S. PATENT DOCUMENTS

| | | |
|---|---|---|
| 8,195,295 B2 | 6/2012 | Stevenson |
| 8,977,355 B2 | 3/2015 | Stevenson et al. |
| 2010/0179619 A1 | 7/2010 | Gray |
| 2013/0345535 A1 | 12/2013 | Elschenbroich |
| 2017/0172647 A1 | 6/2017 | Morgan et al. |

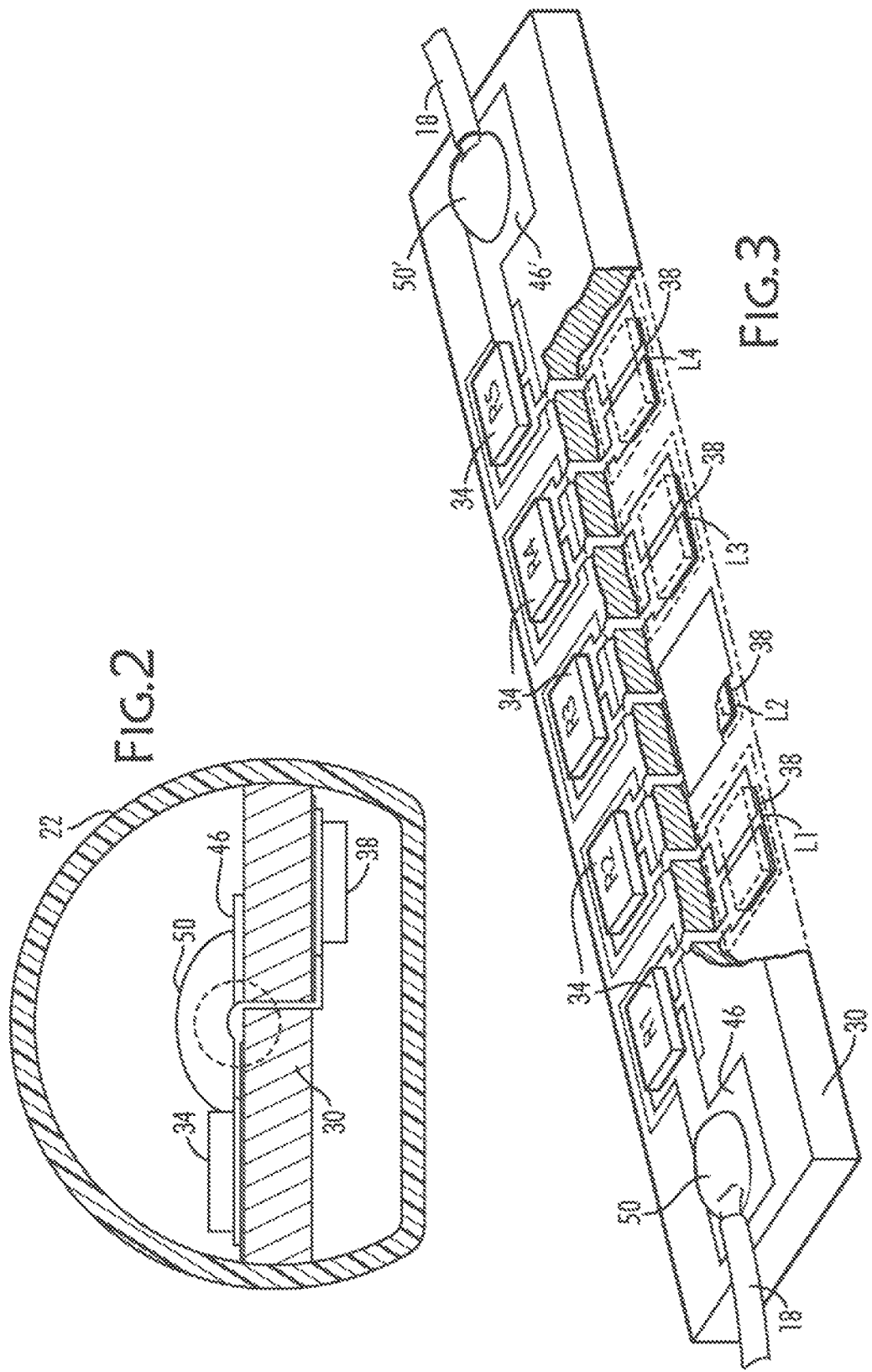

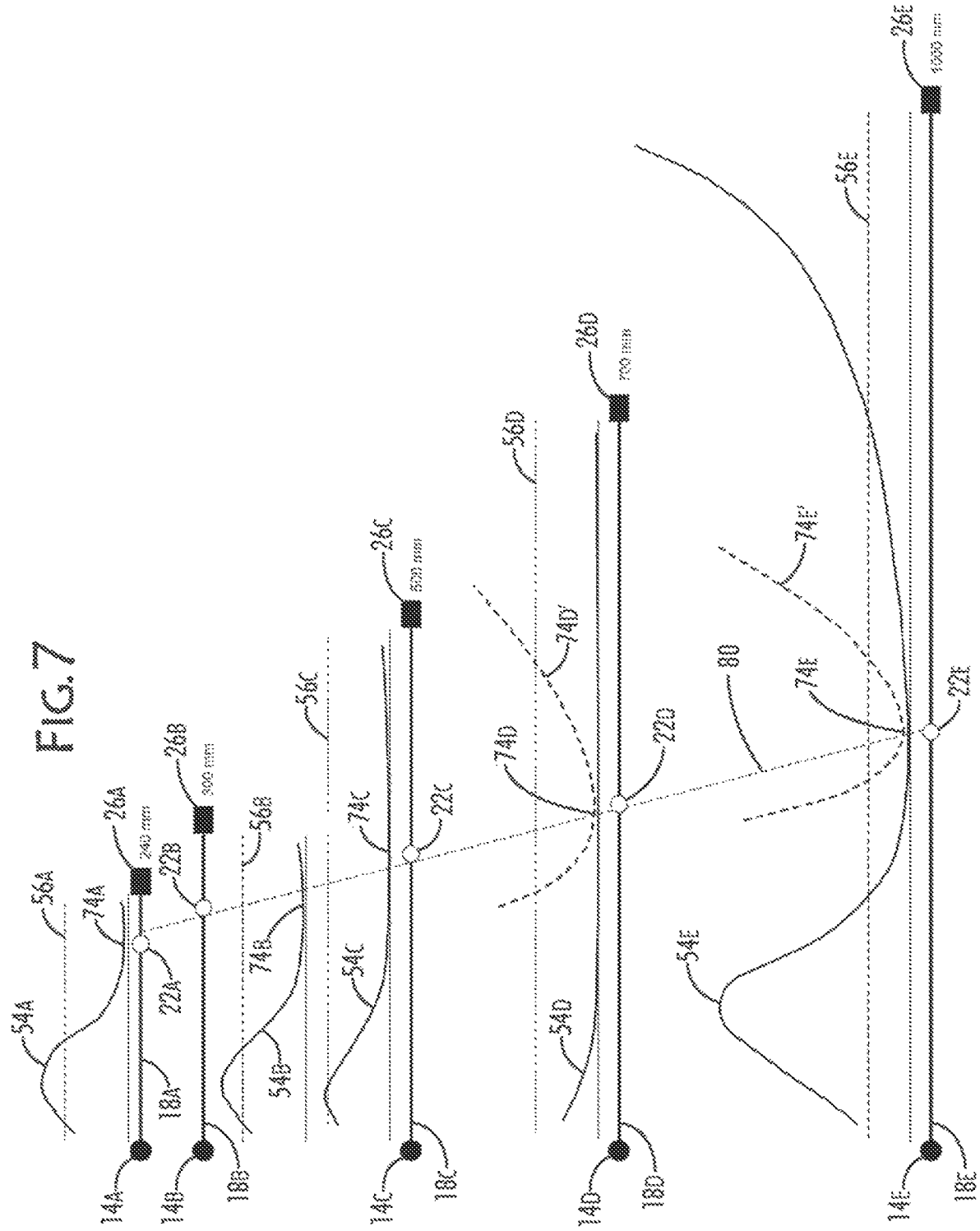

NEUROLOGICAL ELECTRODE SYSTEM FOR MAGNETIC RESONANCE ENVIRONMENTS

CROSS REFERENCE TO RELATED APPLICATIONS

This application is a continuation of and claims the benefit and priority of U.S. patent application Ser. No. 17/021,044, filed on Jan. 15, 2020, entitled "NEUROLOGICAL MONITORING CABLE FOR MAGNETIC RESONANCE ENVIRONMENTS" which further claims the benefit and priority of U.S. Provisional Patent Application No. 62/793,173, filed on Jan. 16, 2020, entitled "NEUROLOGICAL MONITORING CABLE FOR MAGNETIC RESONANCE ENVIRONMENTS" the contents of which are herein incorporated by reference.

TECHNOLOGY FIELD

This disclosure relates to the use of electroencephalograph electrodes in magnetic resonance environments.

BACKGROUND

Electroencephalograph (EEG) electrodes are used in neurological monitoring. An EEG electrode is part of a system that includes the electrode, a cable and a connector. The electrode is attached to the patient and picks up electrical signals in the brain or stimulates nerves in the brain; the cable is attached to the electrode at one end and to an amplifier via the connector.

If the cable is in the presence of a magnetic field oscillating at a radio frequency (RF), such as that generated by a Magnetic Resonance Imaging (MRI) machine, the cable tends to act as an antenna and conducts the radio frequency (RF) energy. The RF energy in the cable heats the cable and any electrically resistive material connected to it. If the cable is connected to an electrode attached to the skin of the patient, resistance heating at the skin-electrode interface may result in a burn injury.

MRI monitoring is a common hospital procedure, so procedures and precautions are taken around MRI machines to avoid such injuries. Ironically, the stronger the magnetic field and the higher the radio frequency, the better the image quality obtained from MR imagine but also the greater the resistance heating and the potential for burns.

Because of the danger of MRI burns to a patient who requires neurological monitoring and is to undergo MRI procedures, the electrodes are normally removed from the patient prior to the imaging procedure, and then re-attached afterwards. Attaching and re-attaching electrodes to patients is done by technicians, and the task is time-consuming and expensive. Moreover, the patient is not being monitored when undergoing the MRI procedure.

There are, however, electrode systems that may remain attached to the patient's head during MR imaging subject to conditions. These electrode systems are typically referred to as "MRI-conditional." The conditions on use of these electrodes may include limits on the strength of the magnetic field of the MR imaging device and the time the patient may remain in the magnetic field attached these electrode systems. MRI conditional electrode systems may use different materials that respond less to magnetic fields, for example, or use tank filters (inductor-capacitor circuits) inserted into the electrode cables to block unwanted RF energy. Unfortunately, tank filters are frequency-specific, so they are not always effective in reducing heating when used in MRI machines. The need to tune these filters individually to the precise frequencies used in MRI also makes them relatively costly and labor-intensive to build.

As a result, there continues to be a need for better ways to avoid or minimize RF heating in electrode systems attached to the patient during MR imaging.

SUMMARY

According to its major aspects and briefly recited, it has been found that a combination of inductors and resistors inserted in-line at an optimal position in the cable of the electrode system forms a radio frequency filter that reduces heating and is less frequency-specific than a tank filter.

An aspect of the disclosure is that the components of the present in-line filter do not include tank filters with their need for precise tuning.

An aspect of the disclosure is that the values and numbers of the resistors and inductors for the in-line filter are selected to reduce radio frequency (RF) power in the electrode system and especially heat dissipation into the skin beneath and near the electrodes.

An aspect of the disclosure is that the values and arrangement of components for the in-line filter are selected to reduce RF power in the electrode system, and reduce excessive heating, through an alternating relationship of resistors and inductors.

Another aspect of the disclosure is that the choice of location in the cable for the in-line components is selected to reduce RF power in that electrode system.

An aspect of the disclosure is that the choices of location, the numbers and component types and values, and arrangement for the in-line RF filter in the cable are selected to reduce the RF power over a broad range of radio frequencies.

Another aspect of the disclosure is that the components of the in-line RF filter may be stock-valued components.

An aspect of the disclosure is that the present RF filter is comprised of miniature, leadless surface-mountable components enclosed by biocompatible, electrically-insulating material comprising a small in-line filter module.

Another aspect of the disclosure is that all module materials and filter components are chosen to contain either no magnetic material at all, or at least the minimum feasible quantity of such material including nickel plating, thus minimizing the risk of dangerous attraction in very strong magnetic fields.

An aspect of the disclosure is the use of approximately 1000 ohms of resistance or less in the present RF filter, as required for optimal performance in a typical EEG amplifier.

Another aspect of the disclosure is the use of ferrite-free inductors in the RF filter, thus minimizing not only the risk of dangerous attraction but also that of magnetic saturation altering the properties of ferrites in strong magnetic fields.

Another aspect of the disclosure is that the total inductance of the in-line RF filter may lie between one and two microhenries, readily achieved without the use of magnetic material.

An aspect of the disclosure is an RF filter included in a neurological electrode system having at least one resistor in series with at least one inductor in-line in the RF filter.

Another aspect of the disclosure is that the components are constructed as a miniature filter module for in-line use in the electrode cable.

Still another aspect of the disclosure is that for a designed in-line filter module located between the first end and the second end of said cable, at a location found by antenna system simulation in software and then improved through a modest amount of real-world experimentation, at least one improved location of said filter module will reduce the coupling of RF energy into the skin of the patient, thus reducing the danger of burns.

Still another aspect of the disclosure is that, for cables within the range of 240 millimeters to 1000 millimeters (one meter) inclusive and using the miniature filter model described in an embodiment of the radio frequency attenuator, the improved location may be determined using a simple mathematical formula.

An aspect of the disclosure is that the in-line filter module may contain an alternating and substantially linear arrangement of resistors and inductors electrically connected in series.

Another aspect of the disclosure is that resistance, and thus power dissipation, in the in-line RF filter is divided among a multiplicity of resistors all having the same or closely similar stock values, thus further reducing heat dissipation at any one location along the filter.

Still another aspect of the disclosure is that the needed inductance in the in-line RF filter is achieved using a multiplicity of ferrite-free inductors, all having the same or closely similar stock values, and further acting as spacers between the heat-generating resistors.

Another aspect of the disclosure is that the number of resistors desirably exceeds the number of inductors by one, so resistors appear at both ends of the linear arrangement. In other words, if a number N of ferrite-free inductors is required to achieve the needed total inductance, the number of resistors will desirably be N+1.

An aspect of the disclosure is that the in-line filter module has contacts on the ends to connect the in-line filter module with the cable. These contacts are preferably comprised of, or at least plated with, copper, silver or gold avoiding the use of nickel or other magnetic materials. Since the wire comprising the cable is likely to be made of carbon fibers instead of copper, and thus not solderable, tin or solder plating is not desirable.

These and other aspects of the disclosure and their features and advantages will be apparent to those skilled in the art of neurological monitoring from a careful reading of the Detailed Description, accompanied by the following drawings.

BRIEF DESCRIPTION OF THE DRAWINGS

FIG. 2 is an end view of a cross section of the in-line RF filter module of FIG. 1;

FIG. 3 is a side perspective view of a double-sided printed circuit board designed for enclosure by the in-line module of FIG. 1, showing an example of the components used therein, according to an aspect of the disclosure;

DISCUSSION OF THE PRIOR ART

Figure 1:
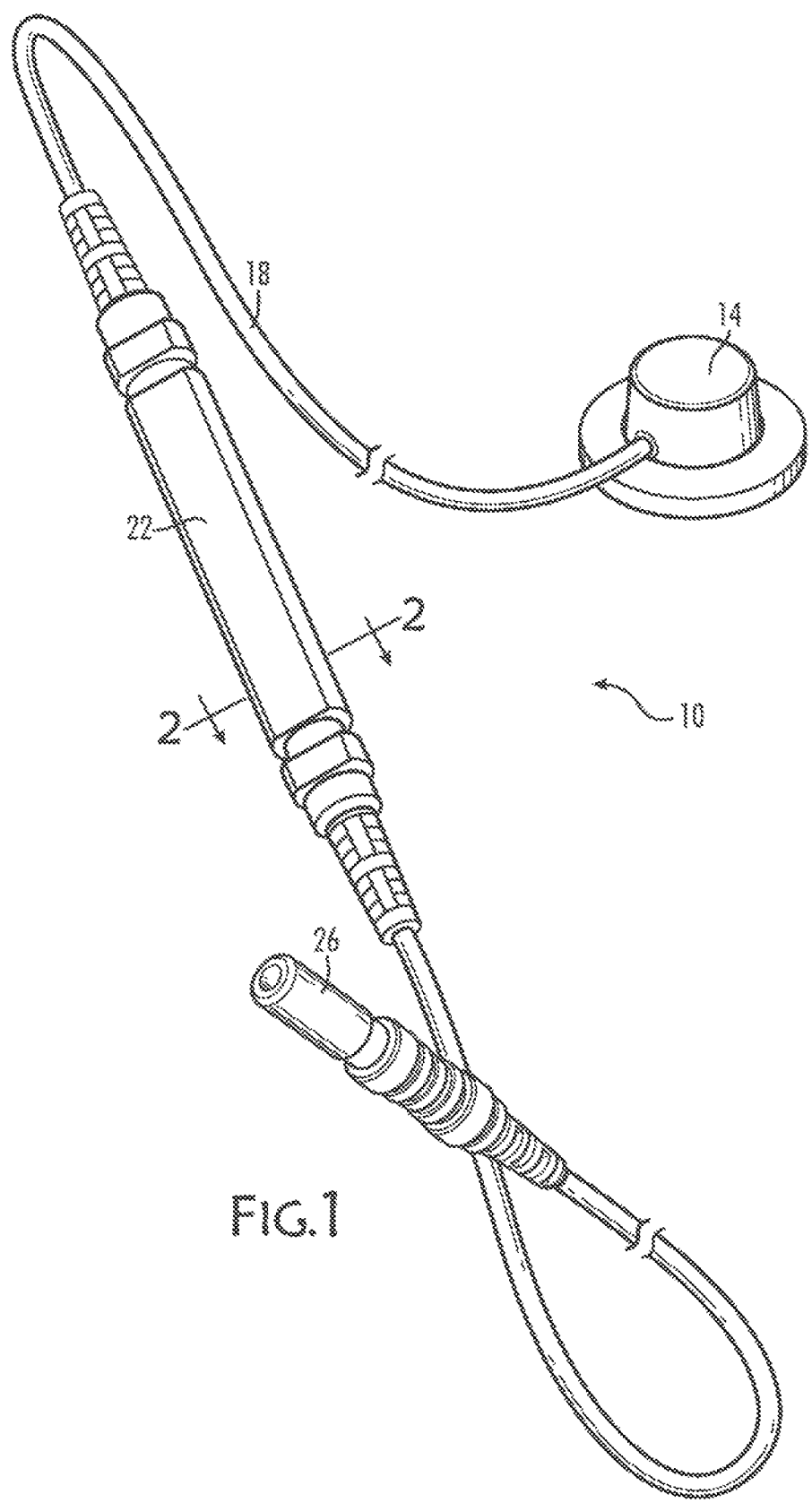
FIG. 1 is a side view of an electrode system including an in-line RF filter module, according to an aspect of the disclosure.

An examination of the prior art in this field showed many U.S. patents already exist, including U.S. Pat. Nos. 7,945, 322; 8,116,862; 8,180,448; 8,200,328; 8,301,243; 8,311, 628; 8,463,375, 8,649,857 and 9,061,139) all by the same inventors (Stevenson et al.) and having the same objective of creating implantable devices using tank circuits to block specific undesirable frequencies.

A tank circuit is the parallel combination of an inductor (unavoidably including some resistance) with a capacitor, which may be discrete such as a manufactured chip or film capacitor or may include other capacitance contributed by nearby objects such as traces or copper areas left on a printed-circuit board. It blocks a typically narrow frequency range centered on $fc=1/2\pi\sqrt{(LC)}$, its resonant center frequency, where fc is the frequency in hertz, L the inductance in henries, and C the capacitance in farads.

For example, an inductor with a value of 390 nanohenries ("L") and a ten-picofarad capacitor ("C") yield fc=80.6 megahertz, close to the FM broadcast band.

The effect of resistance in the tank is to change a parameter "Q," which becomes lower as the resistance increases. High "Q" makes the tank a very effective barrier at fc, with performance falling off sharply as the frequency deviates from it. Low "Q" broadens the frequency response, but at the expense of performance close to fc.

Because it is difficult to control the values of inductors and capacitors precisely, and account for stray capacitance and the effect of magnetic materials in the environment around a tank circuit, some degree of individual adjustment is usually needed to make each tank resonate at the desired fc. This requires the use of tunable components, such as adjustable capacitors, which are far more costly than stock fixed-value ones. The tank must then be isolated from outside effects, which could affect its tuning. In production, this typically adds significant cost. As a further disadvantage, the tank will then block only that one frequency (and a narrow band of others near it) while having little or no effect at others.

The prime object of the invention, therefore, is to provide a barrier against RF energy in EEG electrode leads which avoids the disadvantages of tank circuits by taking a wholly different approach: eliminating the use of parallel capacitance; treating the full electrode, cable and connector together as an antenna-like system at all typically-used MRI radio frequencies; and in that system placing in an optimal position along each cable a filter module comprising lumped inductance and resistance forming a non-resonant filter effective at more than one such frequency, the optimal position being that which causes a minimum amount of RF energy to be delivered to the skin of a patient in contact with the electrode thereby minimizing the danger of burns.

Another object is to provide this RF energy barrier using components able to be used safely in an MRI environment, in the sense of being "MRI conditional" with field strengths and other conditions specified as needed.

A third object is to provide the MRI-compatible barrier using only low-cost, widely-available, stock-valued components requiring no individual adjustment after assembly.

A fourth object is to provide the barrier in the form of a compact filter module which can be mounted in-line in the electrode cables and be safe for use in a medical environment.

A fifth object is to make such a module, and thereby the electrode system containing it, more tolerant of radio-frequency energy and robust against resistance heating than the prior-art electrode systems.

DETAILED DESCRIPTION OF THE INVENTION

A computer model was developed for a set of neurological monitoring electrodes to evaluate RF pickup from an RF device. The model was developed using the commercially-available EZNEC+, Version 6.0 antenna modeling software.

For this model, the electrodes, wires, connectors, and the patient's head are represented as parts of a radio-frequency receiving antenna. The patient's head is divided into nineteen conductive volumes, each with its own resistance and capacitance, to simulate the distribution of radio-frequency current through an extended, electrically resistive load via the skin effect. The external cables are represented by straight wires, dangling wires, or a loop that includes a capacitor representing a multi-electrode connector.

Loads, simulated by two 3000-ohm resistors, simulate the typical resistance between the skin and each electrode. Additional loads, each comprised of inductance and resistance, are modeled in a way permitting easy relocation along the wires to simulate filter modules placed in varying locations.

To simulate the rotating RF field around a patient undergoing MR Imaging, the "birdcage" coil used as an RF source in a typical MRI machine was modeled as a set of four interconnected source dipoles, each dipole being 90 degrees out of phase with the next.

Referring now to FIGS. 1-5, FIG. 1 shows an electrode system 10 including an electrode 14, a cable 18 with an in-line filter module 22, and a connector 26. Cable 18 is in electrical connection with electrode 14 and with connector 26. Electrode 14 may be attached to the head of a patient along with other electrodes for neurological monitoring or other neurological procedure. Connector 26 along with other connectors of other cables are connected to an amplifier (not shown) to amplify the signals received from electrode 14 and which signals traveled through cable 18 and in-line filter module 22.

A cross-sectional view of in-line filter module 22, cut along line 2-2 in FIG. 1, is shown in FIG. 2. In-line module 22 includes a housing 56 made from a tough, electrically nonconductive and nontoxic polymer such as epoxy, silicone rubber, polyvinyl chloride, polyethylene or polypropylene. Housing 56 contains and protects a substrate 30, such as a small printed-circuit board, which is shown in perspective in FIG. 3, to which are attached plural resistors 34 alternatingly in series with plural inductors 38. Substrate 30 is inserted in-line in cable 18 so cable 18 is electrically connected to both ends of substrate 30 at contact pad 46, 46', with solder, conductive epoxy, graphite-paste "wire glue" or other suitable connecting material 50, 50'. Substrate 30, and thereby in-line filter module 22 is thus in electrical connection with electrode 14 and connector 26.

Figure 4:
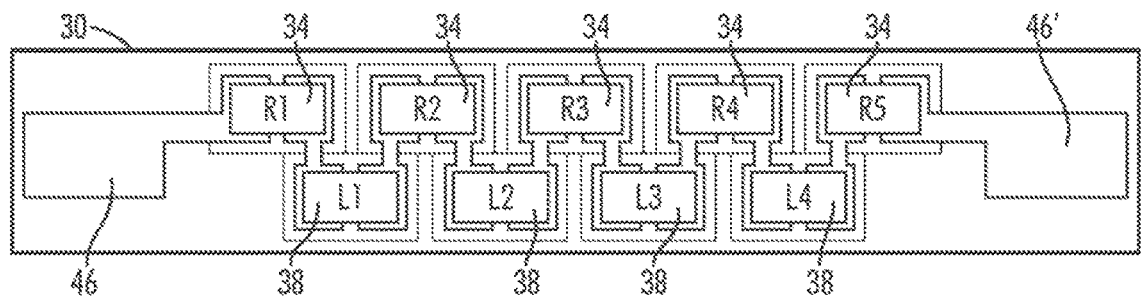
FIG. 4 is a plan view of an alternative, single-sided printed circuit board designed for enclosure by the in-line module of FIG. 1, showing an example of the components used therein, according to an aspect of the disclosure.

In FIGS. 3 and 4, resistors 34 and inductors 38 are shown as they might be mounted on two different types of printed circuit boards: double-sided in FIG. 3 and single-sided in FIG. 4. In each case the number of inductors "N" is four, so the number of resistors "N+1" in an alternating set: resistor 34, inductor 38, resistor 34, inductor 38, and so forth, with all resistors and inductors connected electrically in series. In FIG. 3, the inductors and resistors are placed on opposite sides and connected through vias, while in FIG. 4 all components are on the same side of the board. The latter approach simplifies construction, though at the cost of an increase in overall width.

In any manufacturer's series of standard miniature surface-mount inductors, those with higher inductance values have cores made of ferrite, a magnetic ceramic, while lower-valued ones use nonmagnetic ceramics such as porcelain or alumina. Typically, 390 nanohenries (0.39 microhenries) is the largest value currently made without a ferrite core.

Although comprised chiefly of iron oxide, ferrites come in many compositions optimized for different frequency ranges. They respond strongly to magnetic fields, both by experiencing physical force and by undergoing magnetic saturation which, if the ferrite is used in an inductor, will change the inductor's value. Accordingly, ferrite cores should be avoided in inductors meant for use in strong magnetic fields or near devices, such as MRI equipment, generating them.

In simulation, values of inductance found usable for the invention were in the range of one to two microhenries with an optimal value around 1.56 microhenries (1560 nanohenries). This value is easily achieved by connecting four ferrite-free, off-the-shelf 390-nanohenry miniature inductors electrically in series.

Figure 5:
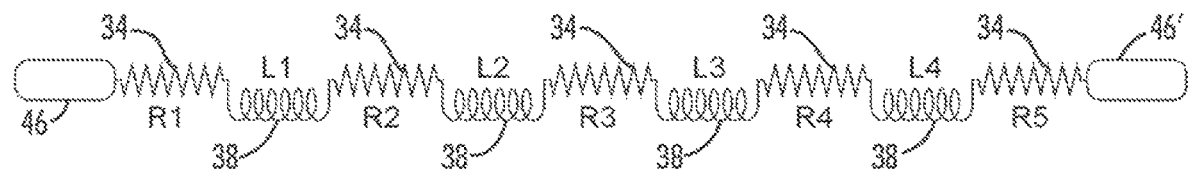
FIG. 5 is an electronic schematic diagram of the filter module according to an aspect of the disclosure.

It is convenient for manufacturing, although otherwise not strictly necessary, to make inductors 38 all have the same nominal value and manufacturer's part number. For a total inductance of 1.56 microhenries, divided among four inductors as shown in FIGS. 3, 4 and 5, this nominal value, as just stated, is 390 nanohenries.

It should be stressed that nominal values include some error and are typically given with tolerances of ±1%, ±5% or the like, so an inductor sold as "390 nanohenries±5%" might have an actual value lying anywhere from 370.5 to 409.5 nanohenries. Differences of this order are often critical to the correct operation of tank circuits, but in the present design should make little difference.

The nominal values of each component type most often manufactured, usually standardized among manufacturers, are known as stock values. 390 nanohenries is an example of such a stock value. It is possible that inductors with different stock values than 390 nanohenries may in some cases be found more convenient to use. For example, advances in miniature inductor technology may yield higher inductance values without using ferrite, thus permitting a needed value to be achieved using a smaller number of physically discrete inductors.

Inductors 38 should be physically spaced a small distance apart so their magnetic fields do not overlap significantly. Such overlap, and the resulting interaction between their fields, could change their effective total inductance. Spacing is conveniently achieved by setting them physically apart in an alternating arrangement with the resistors, as shown in FIGS. 3 and 4. Conveniently, the physically adjacent devices are then connected electrically, again alternating between inductors and resistors, as shown schematically in FIG. 5.

Such an alternating arrangement has the additional advantage of distributing the heat from RF power dissipation in the resistors as widely as possible along the length of the filter module, minimizing potential hot spots. For the latter reason, and since chip resistors are much less costly than miniature inductors, it is desirable—although not strictly necessary—to have one more resistor ("N+1")than inductor ("N") as shown in FIGS. 3, 4 and 5, thus distributing any generated heat more widely.

Resistors may be selected to have a cumulative resistance of up to 1000 ohms, thus remaining within the input requirements for reliable operation of most EEG amplifiers. To allow for resistance in the cable, connections and the inductors themselves, however, it is desirable to make the actual total resistance within the filter module lower. Depending upon the values of those other resistances, a total resistance as low as 1 ohm within the filter module may be found usable.

Just as with the inductors it is convenient for manufacturing, although otherwise not strictly necessary, to make resistors 34 all have the same nominal or stock value and manufacturer's part number.

For example, in a preferred embodiment a filter containing four ("N") 390-nanohenry inductors built according to this invention would include five ("N+1") resistors. Dividing 1000 ohms by five yields 200 ohms. The next few ±1% stock resistor values below 200 ohms are 196, 191, 187, 182 and 180 ohms. One of these values, or possibly one still lower if other resistances in the system are expected to be high, should be selected and may then be optimized by a modest amount of experiment.

A concrete example of in-line filter module 22 according to the preferred embodiment thus includes five resistors 34 each having a resistance of 180 ohms, and four ferrite-free inductors each having an inductance of 0.39 microhenries, arranged in alternation and connected in series beginning and ending with a resistor 34. The complete module thus has a resistance of 900 ohms in series with 1.56 microhenries.

Figure 6:
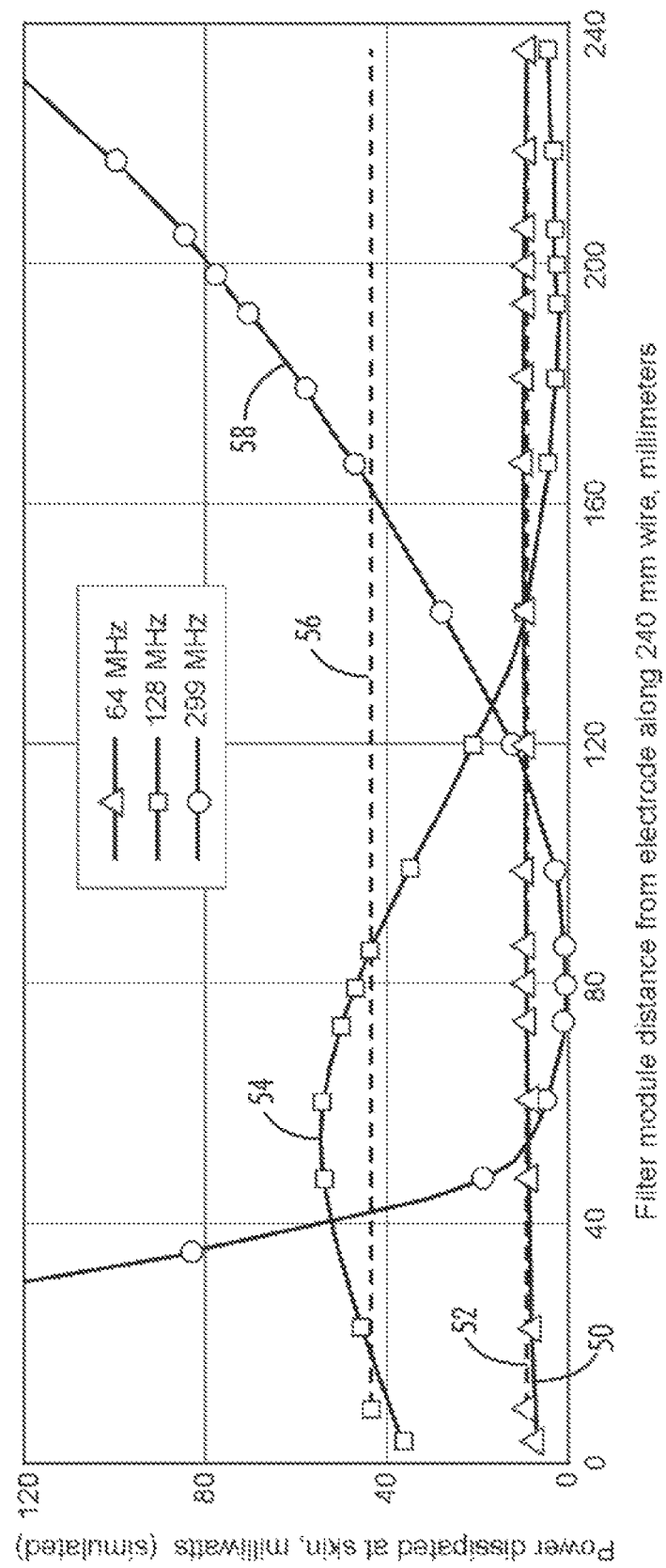
FIG. 6 is a graph of RF power delivered to a patient's skin for three different magnetic resonance radio frequencies when using a simulated in-line filter module placed in one of various locations along a 240-millimeter cable of an electrode system, according to an aspect of the disclosure; and, FIG. 7 is a graph of RF power delivered to a patient's skin at a magnetic resonance radio frequency of 128 MHz, such as used in 3-Tesla MRI machines, placed along cables measuring 240, 300, 500, 700 and 1000 millimeters in length, respectively.

Simulation of the effectiveness of this in-line filter in a cable 18 between an electrode 14 and a connector 26, and exposed to three different commonly-used magnetic resonance frequencies, produced the response curves shown in FIG. 6 as a functions of the location of in-line module 22, embodying the concrete example given, along a cable 18 that is 240 mm long. The horizontal axis represents the distance along the wire from the electrode end, while the vertical axis shows the power delivered to a simulated skin resistance directly under the electrode. To avoid potential burns to the patient, as stated earlier, the prime object of the invention is to minimize this power.

Curve 50, with calculated data points indicated by triangles, shows the delivered power at 64 MHz while for comparison horizontal dashed line 52 shows a constant 8.8 milliwatts, the power with no filter module present. Given that the 240-millimeter wire occupies only 5% of the 4.65-meter wavelength of the 64-MHz RF energy, it functions very poorly as an antenna. Hence, the received and delivered power levels are low and adding the filter module makes little difference. RF burns have been of little concern with 1.5-Tesla MRI machines, which use 64 MHz as the RF frequency.

Increasing the magnetic field strength in an MRI machine improves the image quality and resolution, and to maintain resonance, the RF frequency is increased in proportion. Most new MRI machines operate at three Tesla, requiring a frequency of 128 MHz with a corresponding wavelength of 2.33 meters. Here the 240-millimeter wire occupies about 10% of the 2.33-meter wavelength, functioning much better as an antenna. This raises a definite concern of injury to a patient from RF energy.

Curve 54 shows the delivered power, while again for comparison dashed line 56 shows the power with no filter module present. As is readily seen, with no filtering the power at 128 MHz, 43.8 milliwatts, is nearly five times what was seen at 64 MHz.

At 128 MHz a filter module according to the preferred embodiment now has a strong effect on the delivered power, either raising or lowering it depending on the module's position. The region in which the module can be located to reduce the delivered power is surprisingly broad compared to the wire's length, and the amount of reduction at the minimum point is very substantial. For example, in a 240-millimeter wire, the minimum occurs with the module about 190 millimeters from the electrode, with delivered power of just 2.56 milliwatts: only 6% of the value without the module present.

Experimental MRI machines now in development use still stronger magnetic fields, typically of seven Tesla thus requiring an RF frequency of 299 MHz. Since at this frequency the 240-millimeter wire is nearly one-quarter wavelength, it picks up RF energy very efficiently.

Curve 58 shows a part of the resulting delivered power response, which extends far off the top of the chart at both ends. The power level without filtering, 3.18 watts, cannot be shown for comparison without expanding the graph and could easily be enough to cause serious injury to a patient. Installing the preferred embodiment of the filter module 80 millimeters from the electrode substantially reduces this power level to just 0.48 milliwatt: 0.015% of the unfiltered value.

FIG. 7 shows the same curves for the three-Tesla frequency of 128 MHz only, for varying lengths of wire measuring 240, 300, 500, 700 and 1000 millimeters in length, respectively. Wires 18a-18e are depicted to scale, with electrodes 14a-14e at left and connectors 26a-26e at right.

Curve 54a reproduces curve 54 in FIG. 6 for the 240-millimeter wire showing power dissipated at the patient's skin as a function of the location of filter module 22, while dashed curve 56a reproduces line 56 showing the power with no filtering. Curves 54b, 54c, 54d and 54e, and dashed curves 56b, 56c, 56d and 56e, show the corresponding power curves and unfiltered power levels in the 300-, 500-, 700- and 1000-millimeter wires respectively.

As can be seen in FIG. 7, for each power curve a broad minimum appears, containing within it a point 74a, 74b, 74c, 74d or 74e at which the delivered power is minimized. For curves 74d and 74e, representing the delivered power for the 700- and 1000-millimeter wires, a dashed line 74d' or 74e' has been added magnifying a portion of each curve to show the minimum more clearly.

If filter modules 22a, 22b and so forth are drawn on each wire 18a, 18b and so forth in their correct positions for minimizing the delivered power, it can be seen from FIG. 7 that they fall very nearly on a straight line 80. The slight discrepancy may be due to the finite resolution ("segmentation") of the EZNEC antenna modeling software.

For the concrete example described above, 900 ohms in series with 1.56 microhenries, used at a radio frequency of 128 megahertz, line 80 represents an optimum location for filter module 22 of LM=0.27 L+135, where L is the total length of the electrode system 10, LM is the distance from electrode 14 to the center of module 22, and all distances are expressed in millimeters. Similar formulas can probably be derived for filter modules containing other values of resistance and inductance.

It should be stressed, however, that since computer simulation required some simplifying assumptions the real-life measured curves will likely differ slightly from those shown. Optimization may then be obtained by modest experimentation that is well within the capability of those of ordinary skill in the art.

A series combination of inductors and resistors, without capacitors, when inserted into the cable of the electrode system in the form, for example, of an in-line filter module, forms an effective RF filter that reduces resistance heating at the patient's skin surface under and near the electrodes while being less frequency-specific than a tank filter, able to be made with stock off-the-shelf components, and requiring no individual tuning after assembly.

Optimizing in-line filter module 22 through experimentation on the number and value of the components, which are resistors 34 and inductors 38, and no capacitors; through favoring stock values for resistors 34 and inductors 38; and through favoring positions for in-line module 22 between the ends of cable 18, and generally toward the middle of a 250 centimeter cable; may provide an MRI cable 18 for electrode system 10 that has far fewer restrictions and is more tolerant of radio-frequency energy and robust against resistance heating than prior art electrode systems.

What is claimed is:

1. A neurological electrode system, comprising:
   a magnetic resonance environment with a radio frequency (RF) field;
   an electrode for neurological monitoring;
   a connector configured to connect to an amplifier;
   a cable, having a first end and a second end, the first end in electrical connection to the electrode, the second end in electrical connection to the connector; and
   an inline filter module configured along the cable, the inline filter module comprising one or more inductors and one or more resistors in series, wherein total resistance of the one or more resistors is below 1 ohm, wherein the inductors and resistors are configured in the inline filter module to reduce radio frequency power in the electrode system and the inline filter module limits heat generation in the electrode.

2. The system of claim 1, further comprising two or more inline filter modules configured along the cable.

3. The system of claim 1, further comprising an inline filter module placed between 40 to 80 millimeters along the cable from the electrode.

4. The system of claim 1, further comprising an inline filter module placed between 80 to 120 millimeters along the cable from the electrode.

5. The system of claim 1, further comprising an inline filter module placed between 120 to 160 millimeters along the cable from the electrode.

6. The system of claim 1, further comprising the one or more inductors as a number N of inductors, and further comprising the one or more resistors as a number N+1 of resistors.

7. The system of claim 1, further comprising the one or more inductors spaced a small distance apart and the cable itself is the one or more resistors.

8. The system of claim 1, further comprising having more than one resistor in the one or more resistors, each of the resistors possessing the same resistance as the other resistors.

9. The system of claim 1, further comprising having more than one inductor in the one or more inductors, each of the inductors possessing the same inductance as the other inductors.

10. The system of claim 1, further comprising the one or more inductors having a total inductance between 1 and 2 microhenries.

11. The system of claim 1, further comprising the one or more inductors having a total inductance between 1370 and 1800 nanohenries.

12. The system of claim 1, further comprising the one or more resistors having a total resistance between 0.1 and 1000 ohms.

13. The system of claim 1, further comprising the one or more resistors and the one or more inductors being substantially linear on the cable and electrically connected in series.

14. The system of claim 1, wherein the inline filter does not comprise a capacitor.

15. The system of claim 1, wherein the number of resistors in the inline filter is based on the number of inductors in the inline filter.

16. A neurological electrode system, comprising:
    a magnetic resonance environment with a radio frequency (RF) field;
    an electrode for neurological monitoring;
    a connector configured to connect to an amplifier;
    a cable, having a first end and a second end, the first end in electrical connection to the electrode, the second end in electrical connection to the connector; and
    an inline filter module configured along the cable, the inline filter module comprises one or more resistors and one or more inductors configured in series, and the inline filter module limits heat generation in the electrode.

17. The system of claim 16, further comprising two or more inline filter modules configured along the cable.

18. The system of claim 16, further comprising an inline filter module placed between 40 to 80 millimeters along the cable from the electrode.

19. The system of claim 16, further comprising an inline filter module placed between 80 to 120 millimeters along the cable from the electrode.

20. The system of claim 16, further comprising an inline filter module placed between 120 to 160 millimeters along the cable from the electrode.

21. The system of claim 16, further comprising the one or more inductors as a number N of inductors, and further comprising the one or more resistors as a number N+1 of resistors.

22. The system of claim 16, further comprising having more than one resistor in the one or more resistors, each of the resistors possessing the same resistance as the other resistors.

23. The system of claim 16, further comprising having more than one inductor in the one or more inductors, each of the inductors possessing the same inductance as the other inductors.

* * * * *